United States Patent [19]

Tsunekawa

[11] Patent Number: 5,306,338
[45] Date of Patent: Apr. 26, 1994

[54] DENTAL RESTORATION COMPOSITION

[75] Inventor: Masayoshi Tsunekawa, Toyonaka, Japan

[73] Assignee: Sankin Kogyo K.K., Tokyo, Japan

[21] Appl. No.: 970,635

[22] Filed: Nov. 3, 1992

Related U.S. Application Data

[63] Continuation-in-part of Ser. No. 783,328, Jun. 11, 1992, abandoned, which is a continuation-in-part of Ser. No. 686,685, Apr. 17, 1991, abandoned.

[51] Int. Cl.$^5$ .......................... A61K 6/10; A61K 6/08
[52] U.S. Cl. ......................................... 106/35; 523/116
[58] Field of Search ................. 106/35; 433/228.1; 523/113, 115, 116

[56] References Cited

U.S. PATENT DOCUMENTS

| | | | |
|---|---|---|---|
| 4,525,493 | 6/1983 | Omura et al. | 523/116 |
| 4,872,936 | 10/1989 | Engelbrecht | 156/307 |

FOREIGN PATENT DOCUMENTS

| | | | |
|---|---|---|---|
| 84300358.3 | 1/1984 | European Pat. Off. | C09J 3/14 |
| 84300528.1 | 1/1984 | European Pat. Off. | C09J 3/14 |
| 89118808.8 | 10/1989 | European Pat. Off. | A61K 6/08 |
| 57-16736 | 4/1982 | Japan . | |
| 57-56490 | 5/1982 | Japan . | |

*Primary Examiner*—Linda Skaling
*Assistant Examiner*—Margaret Einsmann
*Attorney, Agent, or Firm*—Jack C. Munro

[57] ABSTRACT

A two-part dental restoration composition composed of a powder and a liquid which are to be combined and evenly mixed prior to usage. The powder is composed of a fluoride containing and releasing glass having an average particulate size under one micron, an aromatic sulfinic acid or its salt and a tertiary amine. The liquid is composed of water-soluble methacryloxyalkyl phosphate, dimethacrylates, diluent monomers and a photo-initiator.

8 Claims, No Drawings ns is not obtained and also a good seal between the amalgam and the tooth is not obtained which substantally prevents ingress of mouth fluids and bacteria into the filled cavity (microleakage) and thus prevents further decay of the teeth. Thus, marginal microleakage has been an inherent problem in conjunction with amalgam restorations. Amalgam also requires cavity preparations plus usage of a retention form which can cause damage to non-carious tooth structure.

DENTAL RESTORATION COMPOSITION

REFERENCE TO PRIOR APPLICATION

This application is a continuation-in-part of U.S. application Ser. No. 07/783,328, filed Jun. 11, 1992, by the same title now abandoned, which is a continuation-in-part of U.S. application Ser. No. 07/686,685, filed Apr. 17, 1991, now abandoned.

BACKGROUND OF THE INVENTION

1) Field of the Invention

This invention relates to a light-cured, fluoride-releasing, dental restoration composition effective for filling cavities and bonding composite resin or amalgam to teeth and to achieve a strong bond and reduced marginal microleakage.

2) Description of Prior Art

Amalgam is an exceedingly common product used in filling tooth cavities in human beings. The main constituents of amalgam are mercury and silver. Amalgam had problems because good adhesion between the tooth and the amalgam is not obtained and also a good seal between the amalgam and the tooth is not obtained which substantally prevents ingress of mouth fluids and bacteria into the filled cavity (microleakage) and thus prevents further decay of the teeth. Thus, marginal microleakage has been an inherent problem in conjunction with amalgam restorations. Amalgam also requires cavity preparations plus usage of a retention form which can cause damage to non-carious tooth structure.

It is becoming apparent that a goodly number of individuals are allergic to mercury and are not able to utilize amalgam in their teeth. It has long been known that there is a need for a dental restoration composition which does not include mercury. It has been known to construct dental restoration compositions of a resin composition such as is shown and described in U.S. Pat. No. 4,500,657, inventor Narayang Kumar. A similar composition is discussed within U.S. Pat. No. 4,814,362. Improvements in dental adhesives are discussed in detail within U.S. Pat. Nos. 4,479,782 and 4,657,941. These adhesives are commonly used as cement liners to stop microleakage under restorations. The bonding agent with the cement liner is to adhere to the dentin and reduce pulpal irritation.

Recently, four in number of fluoride-releasing liners have been introduced in the market. These four are sold under the tradenames of TIME LINE, VITRABOND, XR IONOMER and ZIONOMER. These four liners have been developed to overcome the major disadvantage of conventional lining cements which were (1) long-setting time (three to five minutes), (2) surface dissolution upon acid etching, (3) dehydration upon drying of etched enamel and (4) low mechanical strength. These four liners have achieved some success with (1), (2) and (3), but with (4) only limited success has been obtained. Actually, the mechanical strength of these liners is just not adequate for longevity of the restoration utilizing the liners.

Some lining cements require the removal of a dentin smear layer prior to usage. The smear layer is a naturally produced layer during the preparation of the tooth cavity which functions as a natural cavity liner. It has been thought by some that this layer must be removed for optimum bonding. The removal of this dentin smear layer generally increases hypersensitivity.

SUMMARY OF THE INVENTION

The primary objective of the present invention is to develop an effective formulation of a light-cured fluoridereleasing restorative material for adhesion to dentin without requiring the removal of the smear layer and to achieve substantially superior adhesion between the tooth and the filling material with the filling material being effective in substantially eliminating marginal microleakage in conjunction with the cavity within which it is applied.

Another objective of the present invention is to construct a dental restoration composition which can be used both as a cement liner for an amalgam or a composite restoration or as a complete material eliminating the need for the amalgam.

Another objective of the present invention is to arrive at a dental filling composition that requires no enamel etching of teeth, no dentin conditioning of the teeth, no primer or bonding agent application prior to completing of the restoration.

Another objective of the present invention is to produce a dental restoration composition which has significantly increased adhesive characteristics over and above prior art types of dental restoration materials.

Another objective of the present invention is to construct a dental restoration composition which demonstrates significantly less microleakage at the gingival margin than prior art dental restoration materials.

The dental restoration composition of the present invention is composed of a powder and a liquid with approximately 1.00 part powder to be combined with 0.88 parts liquid by weight. A typical powder formulation would be one hundred parts by weight of strontium aluminofluorosilicate glass having an average particle size of under one micron, four parts by weight of p-toluenesulfinic acid sodium salt dihydrate and three parts by weight of 2-methacryloxyethyl p-(dimethylamino) benzoate. A typical formulation for the liquid would be forty parts by weight of tetramethacryloxyethyl pyrophosphate, thirty parts by weight of methacryloxyethyl phosphate, thirty parts by weight of ethoxylated bisphenol A dimethacrylate and 0.26 parts by weight of camphorquinone.

DETAILED DESCRIPTION OF THE INVENTION

The primary substance in the powder is the filler with the preferred filler material comprising strontium aluminofluorosilicate glass. It is considered to be within the scope of this invention that other fillers could be utilized like inorganic fillers such as quartz, zinc oxide and barium sulfate, or organic fillers such as polymethacrylate powder and Teflon powder. It is to be understood the the word "Teflon" is a tradename.

The filler must be non-toxic and insoluble in saliva, and of a nature such that it imparts a workable viscosity to the composition, in other words, enabling molding and manipulation during application. Suitable fillers are typically inorganic oxides of refractory materials which are clear or white in color. Representative fillers include polymethylmethacrylate, polyethylmethacrylate, quartz powders, silica gel, colloidal silica, glass beads, aluminum oxide, titanium oxide, zirconia, silicate glass, aluminosilicate glass and phosphate glass. The filler should contain leachable fluoride so that it releases fluoride over a prolonged period of use thereby substantially preventing decalcification of the tooth area adhered to. Particular preferred fillers for use are the fluoride-releasing silicates and the preferred material is an aluminofluorosilicate glass such as strontium aluminofluorosilicate. Aluminofluorosilicate glass fillers are available commercially and can be prepared by known methods as described U.S. Pat. No. 4,775,592. See also U.S. Pat. Nos. 3,814,717, 4,360,605 and 4,376,835 for other descriptions of fluoride containing glasses which can be used herein.

It is preferred that the filler material be in the form of relatively small particles having an average size of less than one micron. The smaller the particle size has been found to give rise to better adhesion and also to a higher rate of fluoride-release due to the greater surface area of the smaller particles.

Preparation of the strontium aluminofluorosilicate glass is as follows: The glass was prepared by fusing mixtures of silica, aluminum phosphate, aluminum hydroxide, calcium carbonate, strontium carbonate, strontium nitrate and aluminum fluoride in a platinum crucible at 1350° C., as shown in Table 1. After fusion, the liquid glass was poured from the crucible into water and cooled rapidly. The resultant glass was dried and crushed until it passed through a 350 mesh sieve. The glass was finely ground in a ball mill to less than one micron using isopropyl alcohol as a medium. A silanized glass was prepared in a tumble mixer by combining 100 parts by weight of the glass and 1 part by weight of (gamma)-methacryloxypropyl trimethoxysilane with 200 parts by weight of 0.5% acetic acid containing ethanol solution. The tumbling continued for three hours. After the ethanol was evaporated, the glass was heated to 130° C. for two hours. After crushing and sieving, the following glass composition (Table 1) was obtained:

TABLE 1

| The Glass Composition | |
|---|---|
| Raw Materials | Parts by Weight |
| $SiO_2$ | 35.0 |
| $Al(PO_4)_3$ | 7.0 |
| $Al(OH)_3$ | 9.0 |
| $CaCO_3$ | 10.5 |
| $SrCO_3$ | 21.5 |
| $Sr(NO_3)_2$ | 5.0 |
| $AlF_3$ | 25.0 |

The liquid within the composition of this invention constitutes a light-curable acrylate-based resin. Most preferably, the liquid constitutes about forty-eight percent by weight of the overall weight of the composition. The polymerizable resin contains one or more photopolymerizable dimethacrylate monomers with ethoxylated bisphenol A dimethacrylate being preferred. However, it is considered to be within the scope of this invention that there may be utilized another polymerizable resin, selected from the group consisting of bisphenol A-diglycidyl methacrylate (socalled bis-GMA), bisphenol A dimethacrylate and numerous other dimethacrylates, i.e., virtually any type of dimethacrylate that is usable in dental and orthodontic applications and compositions. The principal function of the resin is to make a solid polymer matrix.

The desirable diluent is tetra-methacryloxyethyl pyrophosphate. The principal function of the diluent is to lower the viscosity of the liquid and thereby is to achieve easy manual mixing. Especially tetra-methacryloxyethyl pyrophosphate is desirable by its high crosslinking property. However, any diluent from the group consisting of urethane dimethacrylate, ethylene glycol dimethacrylate, diethyleneglycol dimethacrylate, triethyleneglycol dimethacrylate, hexanediol dimethacrylate, trimethylolpropane trimethacrylate and neopentylglycol dimethacrylate could be used. Inactive organic solvents could also be used.

Synthesis of tetra-methacryloxyethyl pyrophosphate is as follows: A mixture of 2-hydroxyethyl methacrylate (4 mols) and triethylamine (4 mols) in anhydrous benzene was added dropwise to the anhydrous benzene solution of diphosphoryl chloride (1 mol) at 31 15° C. while stirring vigorously. The mixture was stirred at 0° C. for two hours, and then at room temperature for one hour. After the reaction was completed (heat generation ceased), excessive amounts of water were added to the mixture. The benzene layer was separated, washed with a 5% HCl aqueous solution, saturated $NaHCO_3$ aqueous solution and water. The benzene layer was isolated and dried with anhydrous sodium sulfate. Evaporation of benzene under reduced pressure gave a colorless oil of tetra-methacryloxyethyl pyrophosphate. A small portion of the oil was purified with alumina column chromatography using ethyl acetate-hexane as solvents. The chemical structure was identified by elementary analysis, IR and NMR spectra, calculated as $C_{24}H_{36}O_{15}P_2$.

Another constituent of the liquid is a water-soluble methacryloxyalkyl phosphate. The water-soluble methacryloxyalkyl phosphate can also comprise methacryloxymethyl phosphate, methacryloxyethyl phosphate and methacryloxypropyl phosphate. The viscosity of these phosphates is considerably high and therefore it is necessary to add the above-mentioned diluent prior to usage. The function of these phosphate monomers is mainly to assure adhesion to tooth structure.

The proportion of constituents by weight in the liquid is preferred as follows:

| dimethacrylates | 10–60% |
|---|---|
| water-soluble methacryloxyalkyl phosphate | 20–70% |
| diluents | 10–50% |

In the proportion of these monomers, the proportion of water-soluble methacryloxyalkyl phosphate is most important. If the proportion of the phosphate monomer is lower than 20% by weight good results in adhesion and microleakage were not attained and if higher than 70% by weight the strength of the cured mass was low and adhesion was poor. The proportions of dimethacrylates and diluents depended on the properties of the monomers used and the physical state of the ingredients (liquid or powder). The best mode of this invention was attained at the following proportion by weight:

| tetra-methacryloxyethyl pyrophosphate | 40% |
|---|---|
| methacryloxyethyl phosphate | 30% |
| ethoxylated bisphenol A dimethacrylate | 30% |

A phosphor-containing methacrylate monomer is used sometimes in chemical and dental environments. When the water-soluble methacrylated phosphates were used in large portions, the resulting polymer mass after polymerization was water-sensitive and in the form of a soft gel. In some instances the soft gel was not just water-sensitive but was even soluble in water. The proportion of these monomers is usually not more than 10–15% by weight of the total mixture. This percentage is adequate for OH-bearing methacrylated phosphate monomers.

In this invention, the specific proportion of the water-soluble methacryloxyalkyl phosphate is 25 to 70% by weight which is significantly higher than in the prior art. The resulting mass, to which has been added the balance of the ingredients, after curing becomes exceedingly durable. Moreover, the proportion of 25 to 70% by weight enables the mixed paste to be used in the prepared cavities without any prior pretreatment with it being immaterial if a little moisture is on the wall of the cavity.

The composition of this invention contains a photoinitiator and an accelerator effective to catalyze polymerization upon irradiation. The photoinitiator acts as a source of free radicals when the mixed paste of the composition is irradiated with visible light. The photoinitiator of this invention contains an alpha, beta-diketones. Preferred alpha, beta-diketones for use herein are selected from the group consisting of camphorquinone, benzil, biacetyl, 9,10-phenanthroquinone and naphthoquinone. Most preferred for incorporation into the present compositions is camphorquinone. One accelerator usable with this invention is a tertiary amine. Preferred tertiary amines for use herein are selected from the group consisting of N,N-dimethyl-p-toluidine, butyl diethanolamine, N,N-dimethylaminoethyl methacrylate, morpholinoethyl methacrylate, ethyl p-(dimethylamino)benzoate, 2-methacryloxyethyl p-(dimethylamino)benzoate, and (dimethylamino)benzoic acid or its esters. Most preferred for incorporation into the present compositions are ethyl p-(dimethylamino)benzoate and 2-methacryloxyethyl p-(dimethylamino)benzoate. Another accelerator is aromatic sulfinic acid or its salts. Preferred aromatic sulfinic acids for use herein are one or more of p-toluenesulfinic acid, benzenesulfinic acid and alkylated benzenesulfinic acid and their salts. The function of these accelerators are to form radicals which work as the polymerization catalyst and enhance the efficiency of polymerization and to set the mixed paste into a solid mass. The photoinitiator and accelerators are added to the composition respectively approximately 0.13% of an alpha, beta-diketone, approximately 1.5% of a tertiary amine and approximately 2.1% of aromatic sulfinic acid or its salt. The addition of these ingredients to the powder or the liquid is based on the consideration of their stabilities. In this invention, the alpha, beta-diketone is added to liquid and the tertiary amine and aromatic sulfinic acid or its salt are added to the powder.

The composition of this invention, as previously mentioned, is prepared by simply mixing homogeneously the various components with one another. The resin materials are liquid and thus provide a suitable vehicle for the powder type of filler. The powder/liquid ratio is typically 1.0 to 0.88 by weight. The typical time period for the irradiation of the light for curing was forty seconds per restoration.

EXAMPLE 1

The powder and the liquid was formulated as follows:

| POWDER FORMULATION | |
| --- | --- |
| strontium aluminofluorosilicate (silanized) | 100 parts by weight |
| p-toluenesulfinic acid sodium salt dihydrate | 4 parts by weight |
| methacryloxyethyl p-(dimethylamino) benzoate | 3 parts by weight |

These were mixed in a ball mill for 3 hours.

| LIQUID FORMULATION | |
| --- | --- |
| tetra-methacryloxyethyl pyrophosphate | 40 parts by weight |
| methacryloxyethyl phosphate | 30 parts by weight |
| ethoxylated bisphenol A dimethacrylate | 30 parts by weight |
| camphorquinone | 0.26 parts by weight |

These were mixed by vigorous stirring at room temperature for 24 hours.

SHEAR BOND STRENGTH FOR LINER

The powder and liquid were mixed in ratio of 1/0.88 by weight. The shear bond strength to dentin was tested by the following method and compared with four known (prior art) light-cured, fluoride-releasing liners currently on the market.

TESTING METHOD

Extracted human molars stored in a 1% chloramine solution at room temperature were used as test specimens. These specimens were embedded in a fast cure acrylic resin in a cylindrical plastic mold. The crown part of each tooth was removed with a low speed saw. The exposed occlusal part of the dentin surface of the test specimens was ground wet by 800 grit silicon carbide paper on a polishing machine. The embedded teeth were washed in running fluoride-free water and dried with an oil-free air syringe. The adhesion area was defined by using an adhesive water-repellant sticker with a 3 mm diameter opening in its center. A cylindrical plastic tube was placed over the 3 mm opening and fixed with dental wax. An increment of the mixed material was placed in the tube and cured for twenty seconds with a visible light unit. A thin layer of bonding agent (Scotchbond 2 adhesive, 3M) was applied onto the liner surface and light-cured for twenty seconds. Composite resin (Silux, 3M) was then placed in the cylindrical plastic tube. The resin cylinders were light-cured for forty seconds. The test specimens were immersed in distilled water at 37° C. After 24 hours the test specimens were clamped horizontally into the shear adhesion apparatus and loaded parallel to the vertical axis of the restorative resins. Bond strengths were measured by an Instron universal testing machine (Model 1011, Instron Corp., Canton, Mass.) at a crosshead speed of 1 mm/min. Ten specimens were tested for each variable.

RESULTS

Shear bond strengths (MPa) of light-cured fluoride-releasing liners to human dentin after 24 hours in 37° C. water:

| This Invention | Zionomer | XR Ionomer | Vitrabond | Time Line |
| --- | --- | --- | --- | --- |
| 7.5 | 3.8 | 1.9 | 2.2 | 0.0 |

MICROLEAKAGE FOR LINER

The powder and liquid were mixed in ratio of 1/0.88 by weight, and test for microleakage by the following method, and again compared with the aforementioned light-cured, fluoride-releasing liners of the prior art.

TESTING METHOD

Extracted human molars stored under the same conditions as described in the shear bond strength test were used as test specimens. All teeth were examined for areas of decalcification, caries, or restorations, and only sound teeth were selected. Eighty Class V cavities were prepared, one on the buccal and one on the lingual surface of each tooth. The preparations were approximately 1.5 mm deep, 3.5 mm wide, and 2.0 mm high, and all were located at the cemento-enamel junction in cementum or dentin. The cavities were prepared with a No. 56 tungsten carbide fissure bur in an ultra-high-speed handpiece using a water-spray coolant. All cavo-surface margins were finished to a 90° angle with hand instruments. Enamel etching agents and bonding agents were not used so it would not confound the marginal seal evaluation. The cavity preparations on the buccal surface were cement-lined with comparative commercial products in accordance with their manufacturer's instructions. After light curing for twenty seconds, composite resin (Silux, 3M) was placed on the liner surface and then cured for forty seconds. All the lingual surface preparations were restored with the present invention. After immersion in 37° C. water for twenty four hours, all restorations were finished dry with finishing disks to simulate clinical finishing.

To prevent dye penetration in areas other than the exposed margins, the teeth were sealed with nail varnish to within 2 mm of the restoration margins. The tooth apices were sealed with a light-cured composite resin. The teeth were placed into separate nylon mesh bags and thermocycled together for 1000 cycles between 5° C. and 55° C. with a dwell time of thirty seconds at each temperature. After thermocycling was completed, the samples were placed in a 50% aqueous solution of silver nitrate for two hours in the absence of light and then thoroughly rinsed with distilled water. The test samples were placed in photodeveloper solution under a fluorescent light for four hours to develop the penetration pattern, then rinsed thoroughly. The teeth were sectioned longitudinally in a buccolingual direction using an Isomet saw.

The degree of dye penetration in the cavity walls was assessed separately for occlusal and gingival walls using a binocular microscope at 25× magnification. Dye penetration was scored by an examiner who had no knowledge of which material was used for the restoration. For n=0, the amount of microleakage was zero (0). For n=1, microleakage was confined to the enamel. For n=2, microleakage was into the dentin wall. If the microleakage was well into the dentin, n=3. If the microleakage was as far as the bottom of the cavity, n=4.

| Materials | (n) Total | RESULTS 0 | 1 | 2 | 3 | 4 |
|---|---|---|---|---|---|---|
| Microleakage (n) scores of light cured liners at gingival (dentin cementum wall) | | | | | | |
| This Invention | 40 | 35 | 5 | 0 | 0 | 0 |
| Vitrabond | 16 | 10 | 6 | 0 | 0 | 0 |
| Zionomer | 8 | 0 | 1 | 3 | 2 | 2 |
| XR Ionomer | 8 | 2 | 2 | 4 | 0 | 0 |
| Time Line | 8 | 0 | 0 | 0 | 4 | 4 |
| Microleakage (n) scores of light cured liners at occlusal (dentin) | | | | | | |
| This Invention | 40 | 37 | 3 | 0 | 0 | 0 |
| Vitrabond | 16 | 10 | 6 | 0 | 0 | 0 |
| Zionomer | 8 | 8 | 0 | 0 | 0 | 0 |
| XR Ionomer | 8 | 7 | 1 | 0 | 0 | 0 |
| Time Line | 8 | 6 | 0 | 0 | 1 | 1 |

ALTERNATIVE EXAMPLE

Using the same powder and liquid of Example 1, shear bond strength to dentin and microleakage were tested except powder/liquid ratio of 1/0.6 by weight was used. The results were: The shear bond strength of the bonding system to human dentin after 24 hours of immersion in 37° C. water were 85.2 Kgf/cm$_2$.

| (n) | Microleakage Score Total | 0 | 1 | 2 | 3 | 4 |
|---|---|---|---|---|---|---|
| at gingival (dentin cementum) wall | 20 | 15 | 3 | 2 | 0 | 0 |
| at occlusal (enamel) wall | 20 | 18 | 1 | 1 | 0 | 0 |

EXAMPLE 2

| POWDER FORMULATION | |
|---|---|
| Strontium aluminofluorosilicate (silanated) | 90 parts by weight |
| Calcium hydroxide (silanated with 4% gamma-methacryloxypropyl trimethoxysilane) | 10 parts by weight |
| p-Toluenesulfinic acid sodium salt dihydrate | 4 parts by weight |
| 2-Methacryloxyethyl p-(dimethylamino) benzoate | 3 parts by weight |

The compressive strength and pH value were measured. The powder used in these tests had the above formulation. The liquid was the same as in Example 1. Powder/liquid ratio was 1/0.88.

Compressive strength test

The specimens were prepared by filling the mixed material in the cavity, 4 mm in diameter and 5 mm in height, then light-curing with a light-curing unit at upper, lower and lateral surfaces each for forty seconds. Average compressive strength of six specimens was 2096.6 Kgf/cm$^2$.

pH value measurement

Seven disk specimens were made using a Teflon ring, 15 mm in diameter and 1 mm thick. These specimens were polymerized with a visible light-curing unit. After polymerization, a drop of water (50 microliters), was placed onto each disk and then the pH values measured using pH-meter at five, ten, thirty and sixty minutes for twenty-four hours.

The results were as follows:

| Time (min.) | 5 | 10 | 30 | 60 | 24 hours |
|---|---|---|---|---|---|
| pH | 4.5 | 4.9 | 5.5 | 5.9 | 6.9 |

EXAMPLE 3

Using the powder in Example 1 and the liquid of the following formulation, shear bond strength was measured.

| LIQUID FORMULATION | |
|---|---|
| Methacryloxyethyl phosphate | 50 parts by weight |
| Triethyleneglycol dimethacrylate | 40 parts by weight |
| Ethoxylated bisphenol A dimethacrylate | 10 parts by weight |
| Camphorquinone | 0.26 parts by weight |

At powder/liquid ratio of 1/0.9, shear bond strength was 8.0 MPa.

COMPARATIVE EXAMPLE 1

In Example 1, removal of glass filler leaving the combination of monomers, photoinitiator and accelerators resulted in decrease of shear bond strength to 1–2 MPa.

COMPARATIVE EXAMPLE 2

In Example 1, removal of sodium p-toluenesulfinate dihydrate resulted in low shear bond strength.

COMPARATIVE EXAMPLE 3

In Example 1, removal of methacryloxyethyl pyrophosphate resulted in inferior scores in the microleakage test.

COMPARATIVE EXAMPLE 4

In Example 1, removal of tetra-methacryloxyethyl pyrophosphate and ethoxylated bisphenol A dimethacrylate resulted in the disintegration of the light-cured samples after 24 hours of immersion in 37° C. water.

Although the subject matter of this invention is discussed in conjunction with a fluoride-releasing glass particulate, it is considered to be within the scope of this invention to use a non-fluoride-releasing glass particulate. The subject matter of the dental restoration composition of this invention could be utilized whether or not the glass particulate contains or does not contain fluoride.

What is claimed is:

1. A light-curing, fluoride-releasing dental restoration composition, comprising: a powder and a liquid which are mixed together to be used in dental restoration, said powder including a fluoride-releasing glass filler and accelerator, said liquid including dimethacrylate monomers, diluent and 25–70% of water soluble methacryloxyalkyl phosphate and photoinitiator, said diluent comprising tetramethacryloxyethyl pyrophosphate.

2. The dental retoration composition as defined in claim 1 wherein:
said fluoride-releasing glass filler comprising a particulate having an average size not greater than one micron.

3. The dental restoration composition as defined in claim 2 wherein:
said fluoride-releasing glass filler comprising a strontium aluminofluorosilicate glass.

4. The dental restoration composition as defined in claim 1 wherein:
said accelerator comprising a tertiary amine and an aromatic sulfinic acid or its salt.

5. The dental restoration composition as defined in claim 4 wherein:
said tertiary amine comprising one or more selected from the group consisting of N,N-dimethylaminoethyl methacrylate, N,N-dimethyl-p-toluidine, ethyl p-(dimethylamino)benzoate and 2-methacryloxyethyl p-(dimethylamino)benzoate.

6. The dental restoration composition as defined in claim 1 wherein:
said water-soluble methacryloxyalkyl phosphate being methacryloxyethyl phosphate.

7. The dental restoration composition as defined in claim 1 wherein:
said dimethacrylate monomer comprising one and more compounds selected from the group consisting of ethoxylated bisphenol A dimethacrylate, bisphenol A-diglycidyl methacrylate and bisphenol A dimethacrylate.

8. The dental restoration composition as defined in claim 1 wherein:
said photoinitiator being camphorquinone.

* * * * *